United States Patent [19]

Scott

[11] 4,182,319

[45] Jan. 8, 1980

[54] SURGICAL SPLINT

[76] Inventor: Arnett P. Scott, 4829 Fountain Ave., St. Louis, Mo. 63113

[21] Appl. No.: 939,477

[22] Filed: Sep. 5, 1978

[51] Int. Cl.² .............................................. A61F 5/00
[52] U.S. Cl. ..................................................... 128/79
[58] Field of Search ........................ 128/79, 132 R, 87

[56] References Cited

U.S. PATENT DOCUMENTS

| 844,798 | 2/1907 | Hawley | 128/79 |
| 1,362,398 | 12/1920 | Crawford et al. | 128/79 |
| 1,585,861 | 5/1926 | Huff | 128/79 |
| 3,147,486 | 9/1964 | Dreyling | 128/79 |
| 3,759,254 | 9/1973 | Clark | 128/79 |

FOREIGN PATENT DOCUMENTS

| 355410 | 6/1922 | Fed. Rep. of Germany | 128/79 |
| 445166 | 5/1927 | Fed. Rep. of Germany | 128/79 |
| 262494 | 2/1929 | Italy | 128/79 |

Primary Examiner—Lawrence W. Trapp

[57] ABSTRACT

A surgical splint has identical, symmetrical, oppositely disposed longitudinal support members facing surfaces of which are a surface of a continuous, soft, thin elastic web of uniform thinness. The web is bonded to an outer layer of the same or similar elastic, soft material. The web and outer layer extend, at the ends of the members, between the members, forming connecting elastic bands, integral with the support members. Each of the support members has, extending lengthwise of the member, intermediate but short of the sides and ends of the web and outer layer, and sandwiched between the web and outer layer, an envelope of woven fabric within which is a steel stay. The envelope is made up of a web sheet and a smaller outer sheet, and is preferably sealed around its edges and also is sealed within and between the web and outer layer.

10 Claims, 8 Drawing Figures

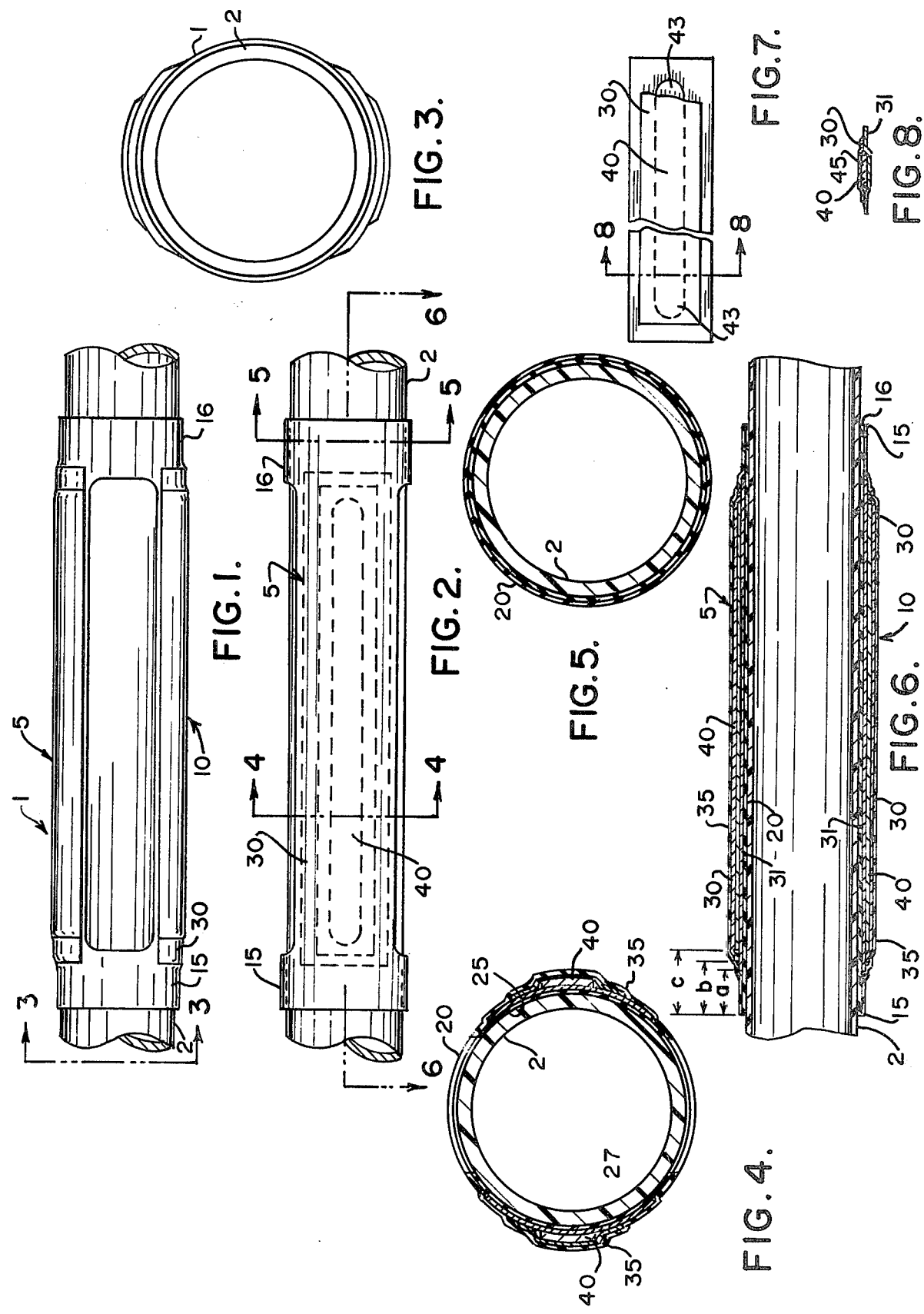

4,182,319

SURGICAL SPLINT

BACKGROUND OF THE INVENTION

The present device is an improvement upon the device shown in my U.S. Pat. No. 3,131,691.

One of the objects of the invention is to provide a splint of the type shown and described in U.S. Pat. No. 3,131,691 which is simpler to manufacture and easier and more effective to employ than such devices known heretofore.

Other objects will occur to those skilled in the art in the light of the following description and accompanying drawing.

SUMMARY OF THE INVENTION

In accordance with this invention, generally stated, a surgical splint or penial appliance is provided which has identical, symmetrical, oppositely disposed longitudinal support members facing surfaces of which are a surface of a continuous, thin elastic web of uniform thickness. The web is overlain by an outer layer coextensive with the web and bonded to the web beyond the boundaries of an enclosed envelope. The web and outer layer, integral with one another, extend, at the ends of the members, between the members, forming connecting elastic bands, integral with the support members. Each of the support members has, on the outer side of the web, and between the web and outer layer, a fabric envelope extending lengthwise of the member, intermediate but short of the sides and ends of the bonded web and outer layer, and sandwiched between the web and outer layer. The envelope contains, sealed within it and within the compass of the web and outer layer, a stay.

The device is provided in discrete lengths, generally from about 7.5 cm to 20.5 cm, in 1.3 cm increments to meet individual requirements but several of the essential absolute dimensions remain within narrow limits. Thus, through the range of lengths from 7.5 cm to 20.5 cm the distance at each end from the far edge of the elastic web inboard to the adjacent edge of the web sheet of the envelope is in the range of 3–10 mm; the distance from the far edge of the elastic web inboard to the adjacent edge of the outer sheet of the envelope is in the range of 6–12 mm; and the distance from the far edge of the elastic web inboard to the adjacent end of the stay is in the range of 12–18 mm. The stays, though of different lengths, can be of the same width. The width of the outer sheet of the envelope can be 12–16 mm; that of the web sheet, 14–22 mm, and that of the elastic web and outer layer, between the bands, 16–24 mm. The thickness of the elastic web is preferably 0.4–1.0 mm.

BRIEF DESCRIPTION OF THE DRAWINGS

In the drawings, FIG. 1 is a view in side elevation of an embodiment of device of this invention, mounted, for purposes of illustration, on a hollow tube;

FIG. 2 is a plan view;

FIG. 3 is an enlarged view in end elevation;

FIG. 4 is an enlarged sectional view taken along the line 4—4 of FIG. 2;

FIG. 5 is an enlarged sectional view taken along the line 5—5 of FIG. 2;

FIG. 6 is a sectional view taken along the line 6—6 of FIG. 2;

FIG. 7 is a top plan view, partly broken away, of an envelope and included stay; and FIG. 8 is a sectional view taken along the line 8—8 of FIG. 7.

DESCRIPTION OF THE PREFERRED EMBODIMENT

Referring now to the drawing for one illustrative embodiment of device of this invention, reference numeral 1 indicates a complete device, shown by way of illustration as mounted on a hollow tube 2. The device is made up of identical support members 5 and 10, connected at their ends by bands 15 and 16.

Facing surfaces 25 and 27 of the support members are parts of an inner surface of an elastic web 20.

The web 20 is thin, elastic, continuous and uniform in thickness. It is made of a sterile latex with an extended elastic limit. The web 20 is overlain by an outer layer 35 of the same sort of material and is bonded to the outer layer beyond the boundaries of an envelope 28. The bands 15 and 16 are integral with the bonded web and outer layer. The bonded web 20 and outer layer 35 thus project at both ends to define a pair of lip sections 17, which are integral with, but slightly narrower in lengthwise extent than the bands 15 and 16. The web sheet of the envelope, as has been stated, extends short of the ends of the device.

The stay 40 is preferably made of thin, flexible steel, covered with a one-piece coating 45.

The envelope 28 is made up of a web sheet 30 and a smaller outer sheet 31, made of woven fabric. The envelope, which in this embodiment is sealed around its edges as well as being sealed within and between the web 20 and outer layer 35, contains within it a stay 40.

The device is dimensioned to meet the specific requirements of its user, in sizes from about 7.5 cm to 20.5 cm in overall length. It has been found, however, that several of the essential absolute dimensions remain within narrow limits. Thus, through the range of lengths from 7.5 cm to 20.5 cm, the distance at each end from the far edge of the elastic web inboard to the adjacent edge of the web sheet of the envelope as indicated by the dimension "a" on FIG. 6, is in the range of 3 mm to 10 mm. The distance from the far edge of the elastic web inboard to the adjacent edge of the outer sheet of the envelope, as indicated by the dimension "b" on FIG. 6, is in the range of 6–12 mm, and the distance from the far edge of the elastic web inboard to the adjacent end of the stay, as indicated by the dimension "c" on FIG. 6, is in the range of 12–18 mm.

The stays, though of different lengths, can be of the same width, preferably on the order of 6 mm. The width of the outer sheet can be 12–16 mm; that of the web sheet, 14–22 mm, and that of the elastic web between the bands, 16–24 mm.

The thickness of the elastic web is preferably on the order of 0.2 to 0.5 mm; that of the stay, on the order of 0.5 mm, with a coating on the order of 0.1 mm, and that of the outer layer, 0.2 to 0.5 mm.

The bands are of the thickness of the combined thicknesses of the elastic web and outer layer, of an axial length between 1.0 and 2.2 cm and of circumferential height between 1.0 and 2.0 cm.

The mode of employment of the device of this invention is substantially the same as that of the device of my U.S. Pat. No. 3,131,691. However, the present device is lighter and simpler to employ, while at the same time it has been found to remain securely in place during use.

The web sheet of the envelope provides stability to the support members against stretching either longitudinally or transversely, without adversely affecting the flexibility thereof.

Having thus described the invention, what is claimed and desired to be secured by Letters Patent of the U.S. is:

1. A penial appliance comprising identical, oppositely disposed, longitudinal support members facing surfaces of which are a surface of a continuous, thin, elastic web of uniform thickness, an outer layer coextensive with, overlying and bonded in its contiguous areas to said web, said bonded web and outer layer extending, at the ends of said support members, between said support members, forming connecting elastic bands integral with said support members, an envelope in each member including a web sheet of woven fabric and a smaller outer sheet of woven fabric, sandwiched between said web and said outer layer, extending lengthwise of each member intermediate but short of the ends and sides of said web and outer layer, and a stay, within said envelope.

2. The appliance of claim 1 wherein the distance at each end from the far edge of the elastic web and outer layer inboard to the adjacent edge of the web sheet, in every length from 7.5 cm to 20.5 cm overall, is in the range of 3–10 mm.

3. The appliance of claim 1 wherein the distance at each end from the far edge of the elastic web and outer layer inboard to the adjacent edge of the outer sheet, in every length from 7.5 cm overall to 20.5 cm, is in the range of 6–12 mm.

4. The appliance of claim 1 wherein the distance at each end from the far edge of the elastic web inboard to the adjacent end of the stay, in every length from 7.5 cm to 20 cm overall, is in the range of 10–20 mm.

5. The appliance of claim 1 wherein the width of the stay in every length of appliance, from 7.5 cm to 20.5 cm overall, is about 6 mm.

6. The appliance of claim 1 wherein the band width in every length of appliance from 7.5 cm to 20.5 cm overall is in the range of 10–20 mm.

7. The appliance of claim 1 wherein the circumferential band height in every length of appliance from 7.5 cm to 20.5 cm overall is in the range of 10–20 mm.

8. The appliance of claim 1 wherein the combined thickness of the elastic web and outer layer in every length of appliance from 7.5 cm to 20.5 cm overall is in the range of 0.5 to 1.0 mm.

9. The appliance of claim 1 wherein the borders of the web sheet and outer sheet of the envelope beyond the stay are bonded to one another.

10. The appliance of claim 1 wherein in every length from 7.5 cm to 20.5 cm overall,
  (1) the distance at each end from the far edge of the elastic web inboard to
    (a) the adjacent edge of the web sheet, is in the range of 3 to 10 mm;
    (b) the adjacent edge of the outer sheet, is in the range of 6 to 12 mm;
    (c) the adjacent end of the stay, is in the range of 10 to 20 mm;
  (2) the width
    (a) of the stay is on the order of 6 mm;
    (b) of the outer sheet, in the range of 12 to 16 mm;
    (c) of the web sheet, in the range of 14–22 mm;
    (d) of the elastic web and outer layer, between the bands, 16 to 24 mm;
    (e) of the bands, axially, 10 to 22 mm;
  (3) the thickness
    (a) of the stay is on the order of 0.2 to 7 mm overall;
    (b) of the bonded elastic web and outer layer, on the order of 0.4 to 1.0 mm; and
  (4) the circumferential height of the bands is in the range of 10 to 20 mm.

* * * * *